United States Patent [19]

Bolduc

[11] Patent Number: 4,611,602

[45] Date of Patent: Sep. 16, 1986

[54] INSTRUMENT AND METHOD OF TUBAL INSUFFLATION

[75] Inventor: Lee R. Bolduc, Raleigh, N.C.

[73] Assignee: BioNexus, Inc., Raleigh, N.C.

[21] Appl. No.: 752,132

[22] Filed: Jul. 5, 1985

Related U.S. Application Data

[63] Continuation-in-part of Ser. No. 632,417, Jul. 19, 1984.

[51] Int. Cl.$^4$ ............................................. A61B 15/00
[52] U.S. Cl. .................................................... 128/747
[58] Field of Search ................ 128/747, 748, 774, 778

[56] References Cited

U.S. PATENT DOCUMENTS 2,441,237  5/1948  Davies ................................. 128/747

*Primary Examiner*—Kyle L. Howell
*Assistant Examiner*—David Shay
*Attorney, Agent, or Firm*—Vidas & Arrett

[57] ABSTRACT

A gaseous dispensing instrument and method for dispensing carbon dioxide gas into the fallopian tube canals of a female is disclosed. The instrument uses a manually operable pump vented to the atmosphere that communicates with a balloon secured to the end of a cannula. Upon insertion of the deflated balloon and cannula through the cervical opening into the uterine cavity, the balloon is expanded and partially withdrawn against the inner walls of the uterine cavity to seal the same. A chamber is charged with carbon dioxide, and upon the balloon being in place in the uterine cavity, gas is released into the uterine cavity and fallopian tube canals through a separate passage in the cannula. After a given period of time, a patency indicator indicating the ratio of carbon dioxide remaining in the chamber compared with the volume introduced therein, indicates and measures any flow of carbon dioxide from the uterine cavity through the fallopian tube canals and informs the operator of the patency of the fallopian tube canals.

12 Claims, 14 Drawing Figures

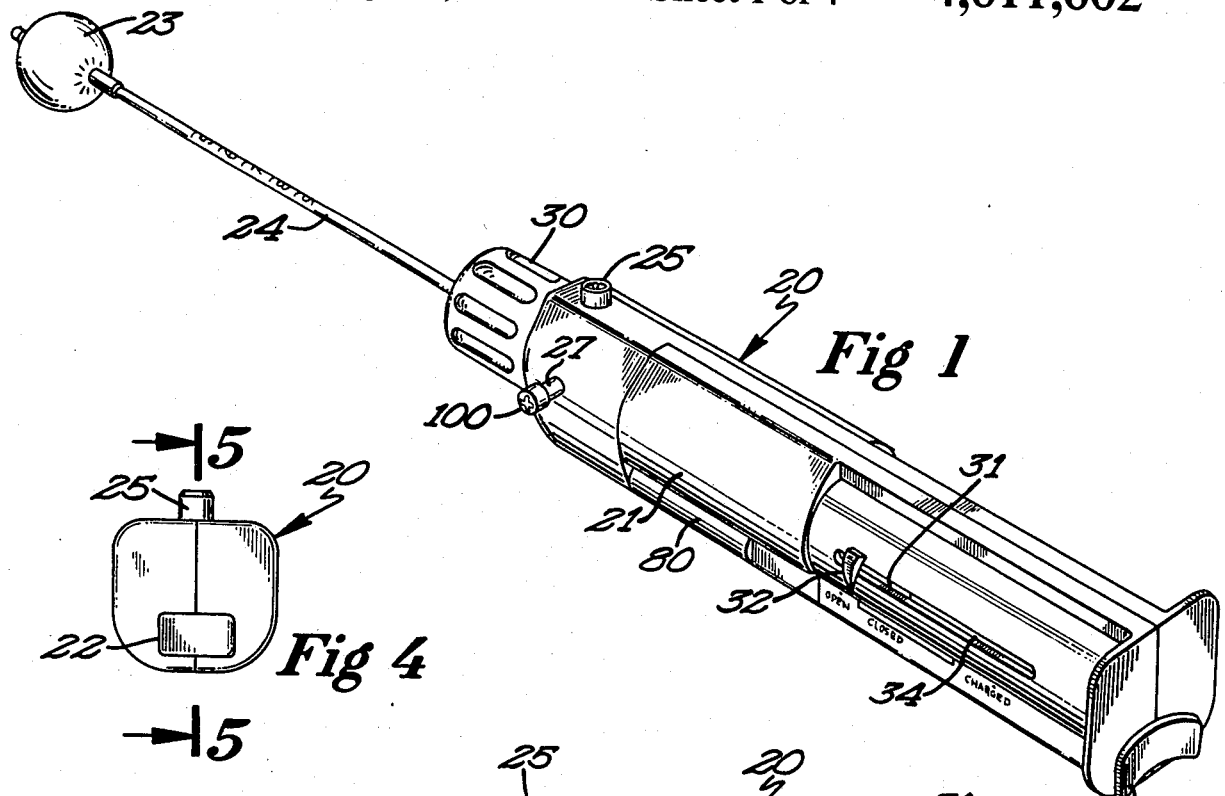
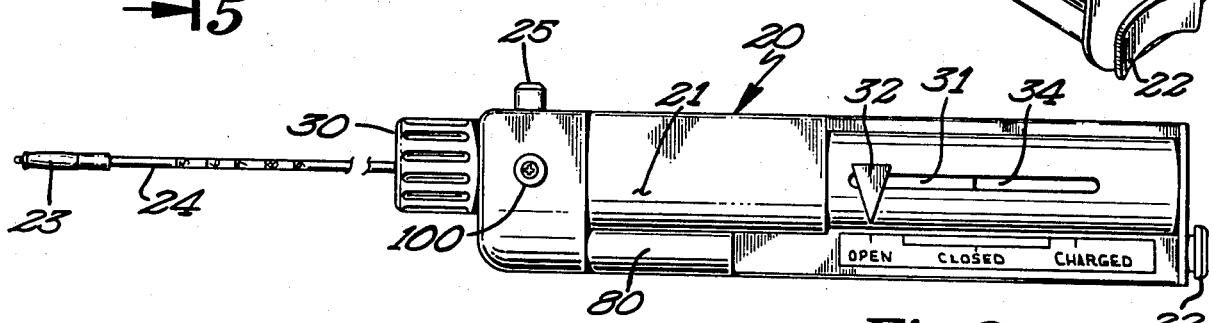
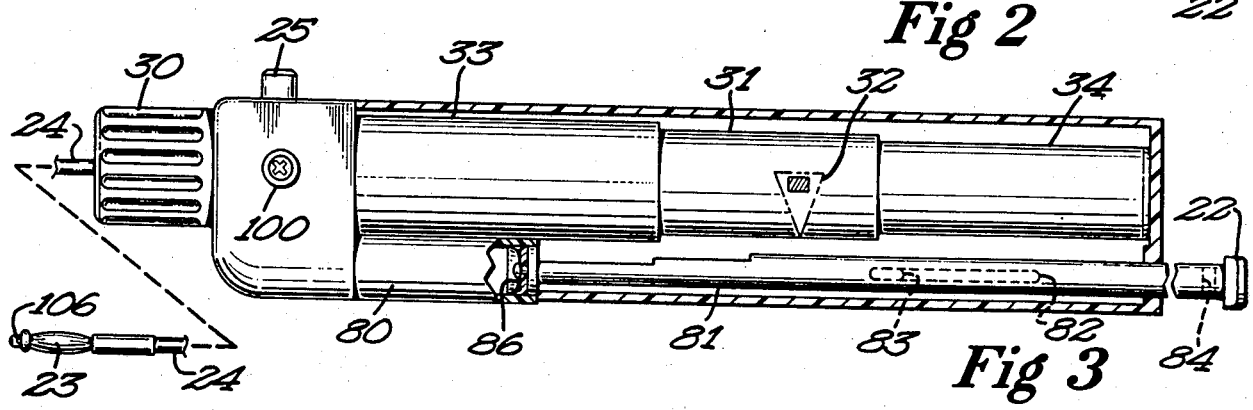
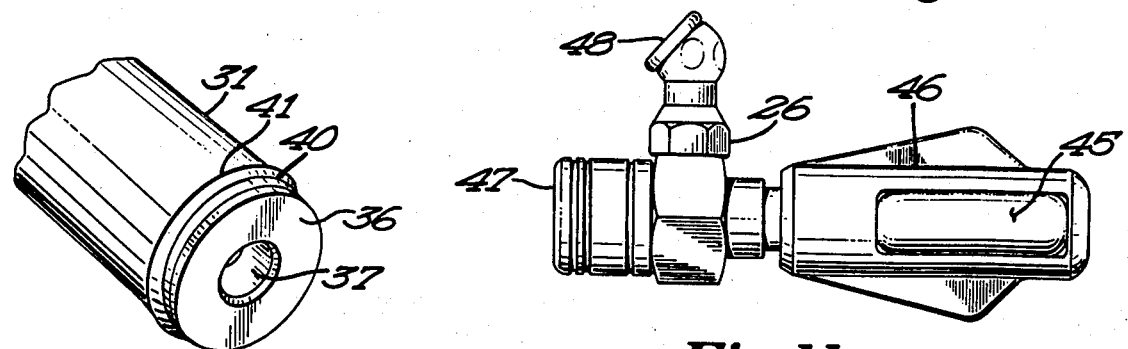

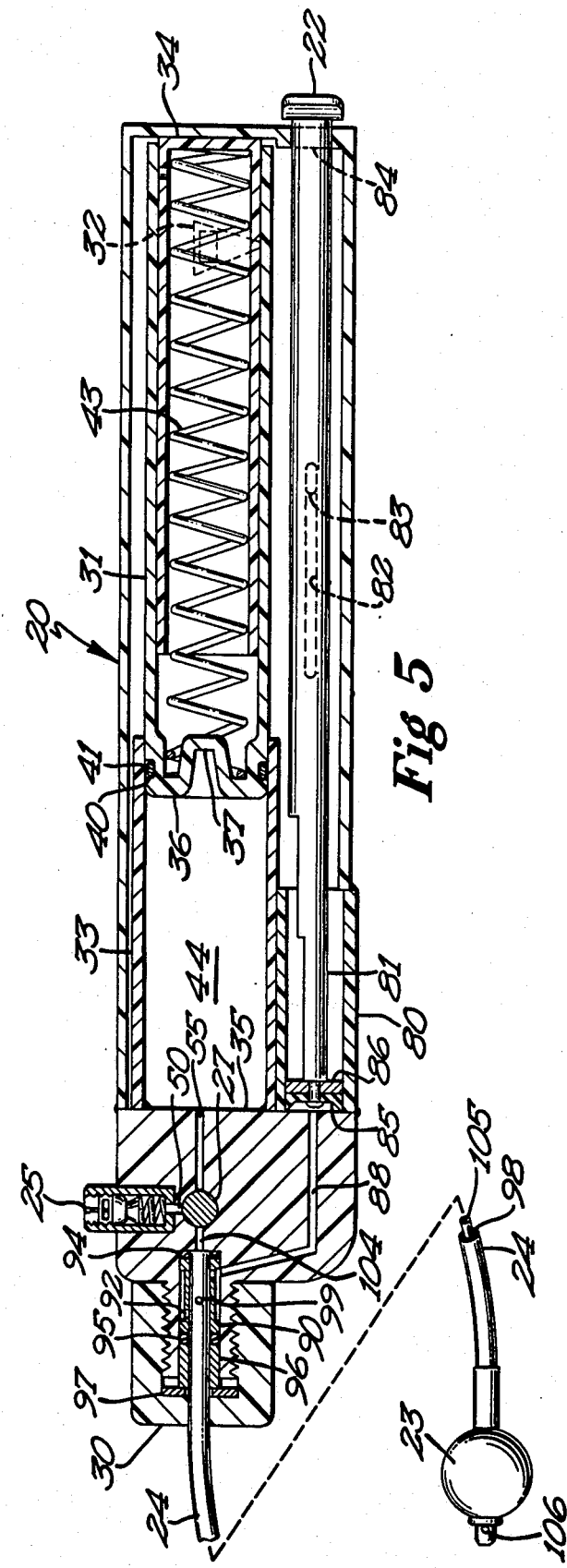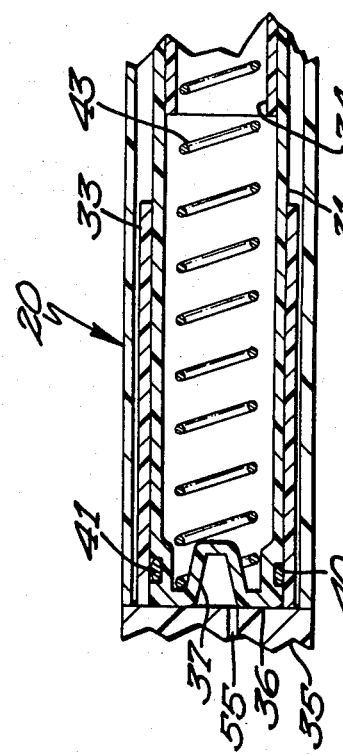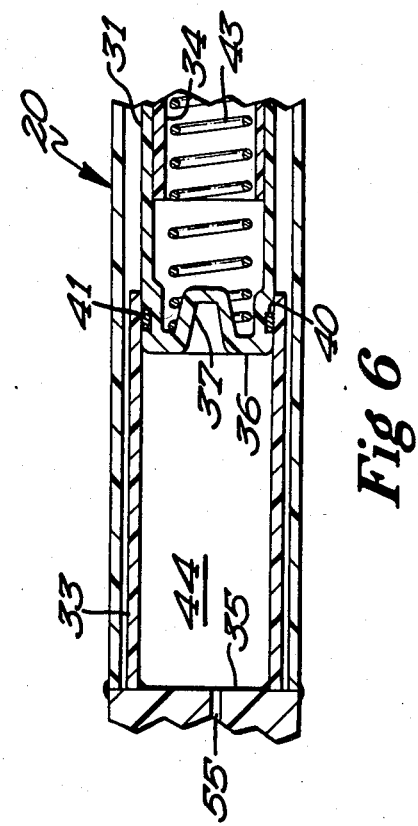

INSTRUMENT AND METHOD OF TUBAL INSUFFLATION

This application is a continuation-in-part of Ser. No. 632,417 filed July 19, 1984.

BACKGROUND OF THE INVENTION

This invention relates to an instrument and method of its use for tubal insufflation of the Fallopian tubes of a female primate.

It is well known that ambient air insufflation may be used to create a pneumoperitoneum in humans. Additionally, the use of gas such as carbon dioxide was first introduced in 1924. However, it was also observed that use of air in the body produces more post operative patient discomfort than carbon dioxide. For a further discussion of the subject, see the article by Diaz, Atwood and Laufe entitled "Laparoscopic Sterilization with Room Air Insufflation: Preliminary Report" appearing in the International Journal of Gynaecol Obstete 18, pages 119–122, 1980.

It has also been observed that carbon dioxide has been used in the Rubin Test and if the tubes are patent, the gas upon leaving the Fallopian tubes, enters the peritoneal cavity. The release of this gas may produce some pain in one or both shoulders of the patient. If the manometer used with the Rubin Test registers less than 100 millimeters Hg, the tubes are patent and if the test shows it to be between 120 and 130 millimeters Hg there may be stenosis or stricture but complete occlusion is not detected. If the test pressure rises to 200 mm. Hg, the fallopian tubes are determined to be completely occluded. A further disclosure of this particular test is found in JAMA, Nov. 4, 1983—Vol. 250 and is a reprint from an article published September, 1920 entitled "The Nonoperative Determination of Patency of Fallopian Tubes" by I. C. Rubin, M.D.

Additionally, there are certain mechanisms and structures disclosed in recent patents which are relevant to the present invention, such as U.S. Pat. No. 4,182,328 by Bolduc and Dickhudt entitled "Dispensing Instrument and Method". This instrument and method dispenses fluids and fluid like materials into the uterus and Fallopian tube canals. The instrument described therein has an elongated probe with a forward end carrying an expandable balloon assembly. A dispensing structure located within the housing of the instrument is used to expand the balloon assembly and discharge drug material into the uterine cavity. The drug material is stored in a container accommodated by the dispensing apparatus.

The teachings of U.S. Pat. No. 4,182,328 are unsuitable for use in determining the patency of the fallopian tubes of a patient. For instance, there is no part of the mechanism adapted to receive a predetermined quantity of gas, nor is there any means visible for detecting the condition of patency of the Fallopian tubes.

It is therefore a general object of this invention to provide an instrument and method of injecting carbon dioxide into the Fallopian tube canals and determining their patency directly from the instrument.

It is still another object to the invention to permit external charging and discharging of the instrument from an external source of gas.

It is a further object of the invention to expand and contract a balloon within the uterine cavity in conducting a patency test upon a female primate.

It is yet another object of the invention to use two separate and distinct supplies of gas in performing the patency test using the invention.

It is still a further object of this invention to permit charging of the instrument with carbon dioxide gas but prevent such charging of the instrument after the gas has been released in the patency test.

It is still a further object of this invention to introduce no more than 55 cubic centimeters of carbon dioxide under a maximum of 200 millimeters of mercury into the uterine cavity and connecting Fallopian tubes.

It is still an object of the invention to provide a patency indicator that has a moving member and an indicia scale to measure the openness of Fallopian tube canals.

It is yet another object of the invention to carry out the steps of injecting the carbon dioxide gas and determining how much gas escapes as a measure of the openness of the Fallopian tubes.

SUMMARY OF THE INVENTION

The invention is directed to an apparatus and method for injecting carbon dioxide into the Fallopian tube canals of a female. An expandable member, and more particularly a balloon, is attached to the end of a cannula that is inserted through the cervical opening into the uterine cavity where the balloon is expanded. The carbon dioxide is injected into a gas dispensing mechanism having a patency indicator connected therewith for indicating the ratio of gas remaining in the dispensing mechanism as compared with the volume of gas initially introduced therein thus measuring any gas flow from the uterine cavity through the Fallopian tube canals in a given time period.

BRIEF DESCRIPTION OF THE INVENTION

A detailed description of one preferred embodiment of the INSTRUMENT AND METHOD OF TUBAL INSUFFLATION is hereafter described with specific reference being made to the drawings in shich:

FIG. 1 is a perspective view of an embodiment of my invention;

FIG. 2 is a side elevation of the embodiment of my invention;

FIG. 3 is a partial side elevation of my invention with the outer housing removed;

FIG. 4 is an end elevation of my invention;

FIG. 5 is a side elevation in cross section of my invention taken across lines 5—5 of FIG. 12. disclosing a curved cannula;

FIG. 6 is a sectional side view of the gas dispensing mechanism in a charged condition;

FIG. 7 is the same sectional side view of the gas dispensing mechanism in a discharged condition;

FIG. 10 is a perspective end view of the piston portion of the gas dispensing mechanism;

FIG. 11 is a side view of the carbon dioxide charging and discharging device;

DETAILED DESCRIPTION OF INVENTION

Figure 13:
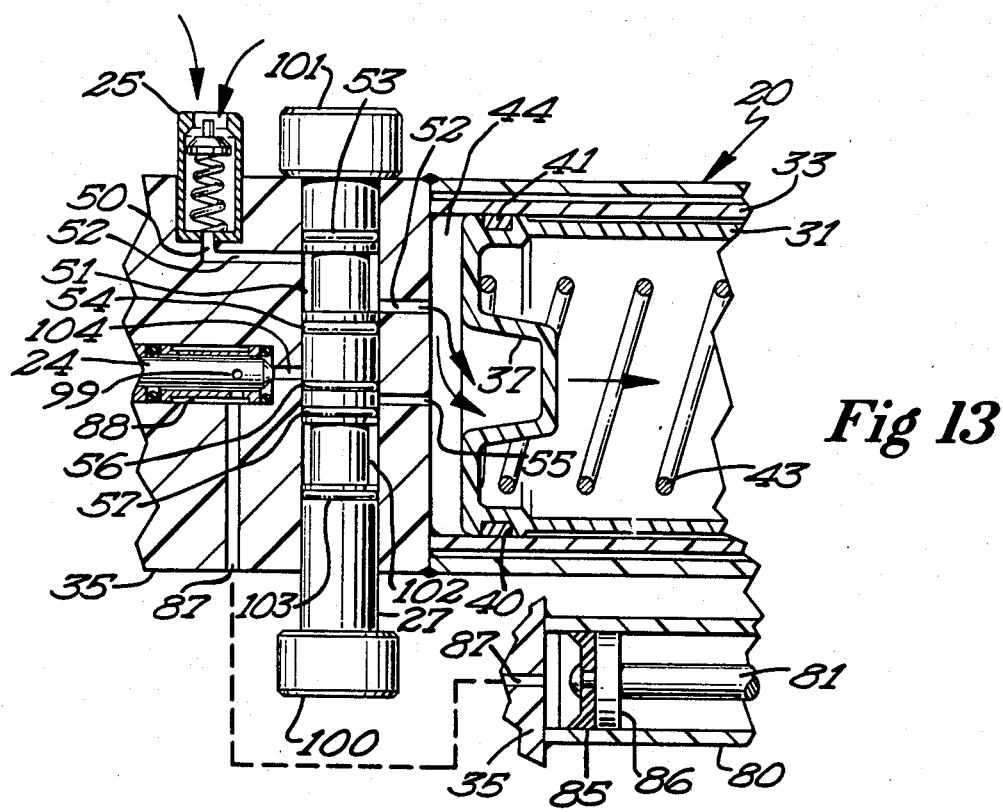
FIG. 13 is a partial top plan section showing the spool valve in a gas charging position; and, FIG. 14 is a partial top plan section showing the spool valve in a gas discharging position.

Referring to the drawings, there is disclosed in FIG. 1 an instrument 20 for tubal insufflation of the Fallopian tubes of a female which is operable to transmit a gas into both canals of the Fallopian tubes of the reproductive system of a female. Instrument 20 has an outer housing 21 that encloses a pump mechanism which has an external plunger handle 22 emerging from the end thereof, the pump being connected to a balloon 23 disposed adjacent the end of a gas dispensing cannula 24. That is, cannula 24 is an elongated flexible probe and is secured to and extends away from the forward end of housing 20 generally along the longitudinal axis of the housing. The instrument 20 has a check valve 25 secured at the top thereof through which an external gas charging and discharging mechanism 26 may be applied (FIG. 11). To further facilitate operation of the instrument 20, a spool valve 27 is disclosed and is shown in FIG. 13 in a position to receive carbon dioxide under pressure through check valve 25. A compression fitting 30 is used to help hold cannula 24 and balloon 23 in place within instrument 20.

When carbon dioxide has been applied to check valve 25 from the gas charging mechanism 26, a hollow piston 31 is moved to the rear of the instrument and carries with it a pointer of indicator 32 to facilitate an easy determination of the condition and position of piston 31. In other words, upon being charged, piston 31 is moved to the right and indicator 32 will appear above the designation "CHARGED".

As shown particularly, in FIGS. 3 through 5, housing 20 has an inside chamber or cavity 33 that accommodates piston 31 and another internal fitting cylinder assembly 34. Thus, piston 31 slides inside cylinder 33 and cylinder 34 slides insides hollow piston 31. (This is best seen in FIG. 5). The forward end of cylinder 33 bears against a fixed transverse wall 35 adjacent the forward end of housing 20. Piston 31 has a closed forward end 36 that is further defined with a well 37 formed therein. The forward facing end of piston 31 has an annular outwardly open groove 40 formed therein accommodating a sealing or "O" ring 41 under compression. Disposed within piston 31 and secured around well 37 is a coiled compression spring 43 that bears against cylinder 34 at the right end portion thereof (FIG. 5). As seen in FIG. 5, "O" ring 41 creates a gaseous seal against the inner wall of cylinder 33 when a compressed gas is introduced into an interior cavity or chamber 44 created by the compression of spring 43.

FIG. 11 is directed to the carbon dioxide gas charging mechanism 26 and is designed to accept carbon dioxide capsules 45 that are held in place by housing 46. Upon housing 46 being tightened, it presses the smaller end of capsule 45 into a gas discharge mechanism. The 700 to 900 psi pressure in the capsule is reduced to approximately 10 to 20 psi through the use of a gas valve regulator 47 that discharges the gas through a nozzle 48 that includes an internal check valve.

Figure 14:
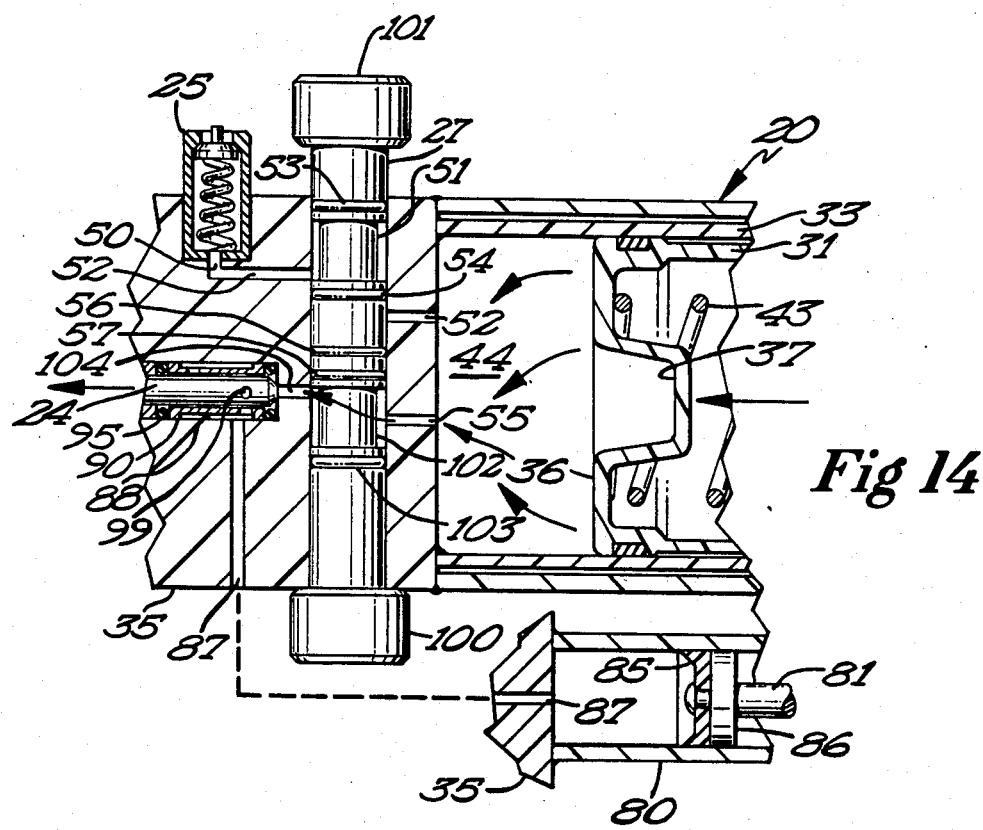

Reference is now made particularly to FIGS. 5, 13 and 14 in which spool valve 27 is disclosed in combination with the other elements through which it works. When the gas charging and discharging mechanism 26 is applied to check valve 25, carbon dioxide passes through check valve 25 into a passage 50 which is directly above the spool valve but is shown rotated 90° schematically in FIGS. 13 and 14. Upon carbon dioxide reaching passage 50, it passes around a reduced diameter concave portion 51 that permits communication with a passageway 52 formed in transverse wall 35. Once the carbon dioxide reaches chamber 44, it reacts against compression spring 43 causing piston 31 to move to the right until it reaches the position shown in FIG. 5 where the instrument is fully charged with carbon dioxide. Upon removal of the gas charging and discharging mechanism 26 from check valve 25, no further activity takes place with respect to the movement of piston 31. A pair of "O" rings 53 and 54 are disposed in annular grooves just outside of the annular chamber created by reduced diameter portion 51.

It will be observed that a return passage 55 formed in transverse wall 35 is blocked to the passage of cargon dioxide gas due to a pair of "O" rings 56 and 57 disposed in annular grooves that appear on opposite sides of passageway 55 on valve 27. That is, "O" rings 56 and 57 form a gas blockage to the movement of any gas through passage 55 in the position shown in FIG. 13.

Figure 8:
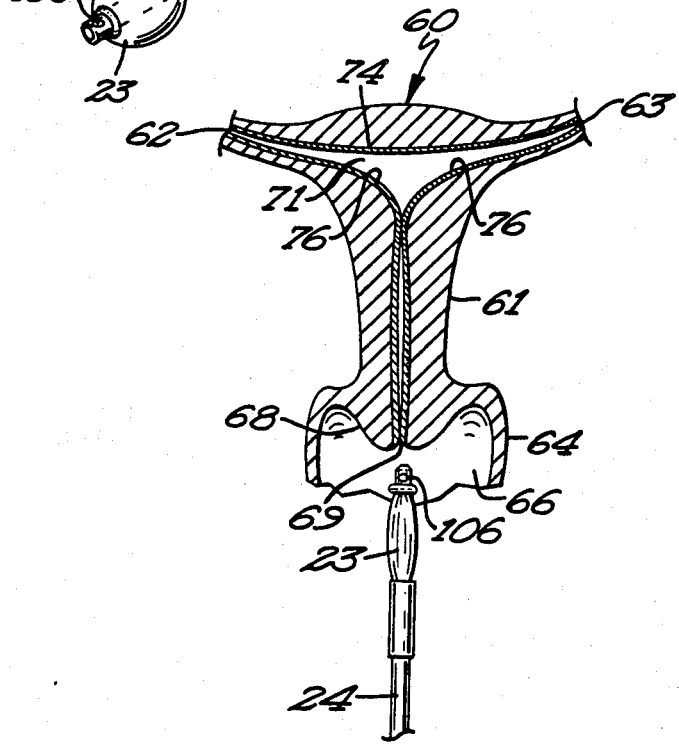
FIG. 8 is a sectional view of the female reproductive organs prior to the insertion of the cannula into the uterine cavity.
Figure 9:
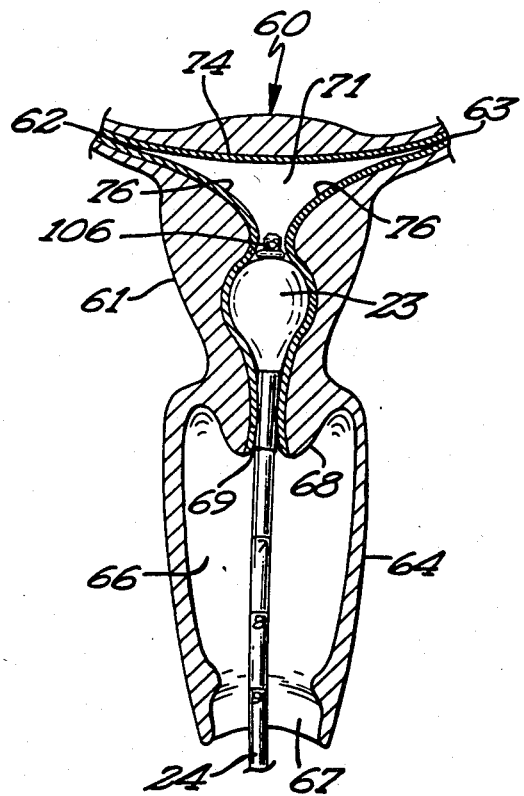
FIG. 9 is a view similar to FIG. 8 with the expanded balloon and cannula inserted into the uterine cavity.

Turning now to the mechanism for creating a means of expansion within the uterine cavity, reference is made to FIGS. 8 and 9 where there is shown a reproductive system of a primate female indicated generally at 60, for receiving the balloon end 23 of cannula 24. The reproductive system 60 has a uterus 61 joined to a pair of Fallopian tubes 62 and 63, in which the lower part of uterus 61 is integral with a vagina 64. Vagina 64 has a vaginal cavity 66 and an entrance or vestibule 67, with the opposite end of vaginal cavity 66 being in communication with a cervix 68. The cervix 68 has a normally closed opening 69 and has a passage from vaginal cavity 66 to the uterine cavity 71. The Fallopian tubes 62 and 63 have passages which communicate with the uterine cavity 71 and has a top wall or fundus 74 that further includes internal side walls 76 which communicate with cervix 68.

The uterine cavity 71 varies as to size and configuration and is generally flat and somewhat triangular in shape.

By reference to FIG. 9, balloon 23 has been inserted through cervical opening 69 and is located in uterine cavity 71. Balloon 23 and cannula 24 may be rotated about the longitudinal axis of cannula 24 during the insertion procedure. Once cannula 24 is inserted in uterine cavity 71 to touch fundus 74, the cannula 24 is partially withdrawn to the general position shown in FIG. 9 where it forms a gaseous seal against inner walls 76 of the uterine cavity 71. Balloon 23 is constructed such that it is much less resilient and flexible than the balloons of U.S. Pat. No. 4,182,328. The function of the present balloon is to provide a pressure seal which prevents air movement through the cervix. It must withstand pressure greater than 200 mm Hg since such pressure will be applied to the uterine cavity by the device. The flexible balloons of U.S. Pat. No. 4,182,328 were designed to stretch over the cannula tip so as to push a plug of material into the uterine cavity. Such balloons could not withstand 200 mm Hg pressure from the inside of the uterine cavity.

Referring primarily to FIGS. 2, 3, 13 and 14, cannula 24 is shown in communication with a pump mechanism 80 that is manually operated through an elongated arm 81 which communicates with element 22. Elongated arm 81 has an elongated slot 82 formed longitudinally therein that engages a stop member 83 in slot 82, that is anchored to housing 20. In other words, the length of stroke of plunger 81 is controlled through elongated slot 82 and upon push rod 81 being extended internally to its maximum position, a slot 84 formed transversely in the end of push rod 81 may be used to lock the push rod in place. That is, cylinder 80 forming a postion of the pump has a sealing member 85 secured to its end piston member 86 so that upon withdrawal of push rod 81, a vacuum is created in a line 87 leading from cylinder 80 which is in fluid communication with a bore 88 formed in the end of transverse wall 35.

Figure 12:
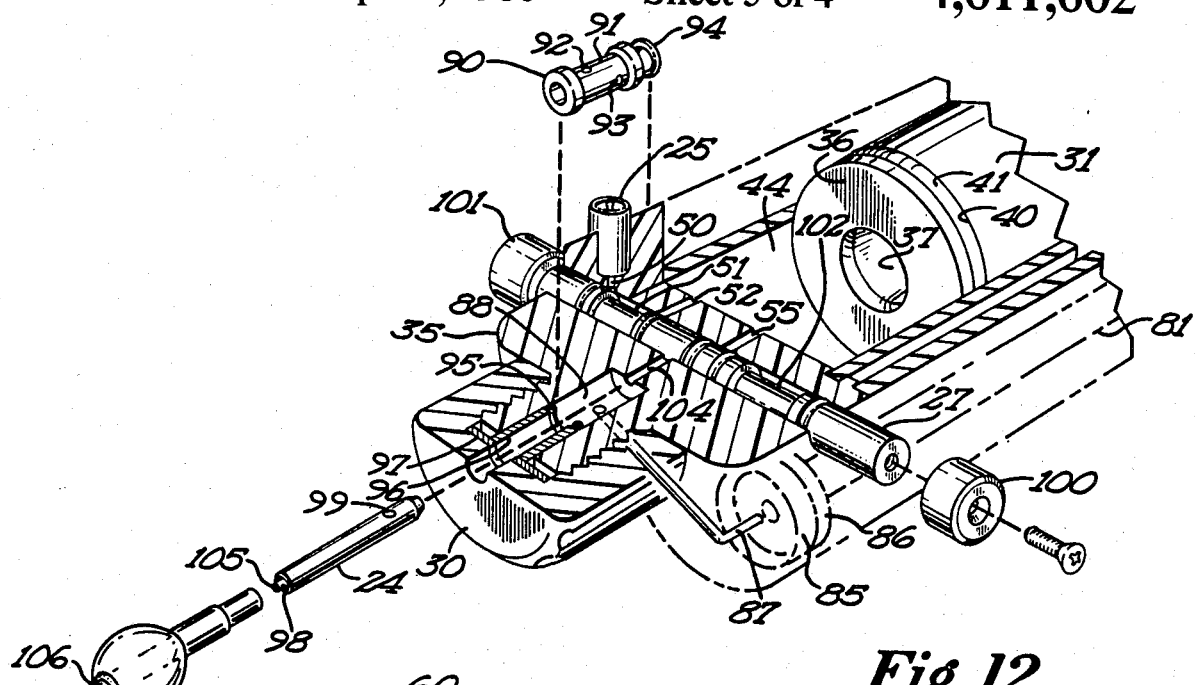
FIG. 12 is a partial diagramatic end view showing the gas spool valve.

A collar 90 (FIG. 12) is disposed in bore 88 and has a reduced spool diameter 91 formed therein through which a pair of transverse bores 92 and 93 are formed. Also disposed in bore 88 are a pair of "O" rings 94 and 95 that are disposed longitudinally at the innermost end and outermost end of collar 90 where "O" ring 95 is also in communication with a sleeve 96 that also resides in bore 88. Disposed at the outer end of sleeve 96, is a flat circular washer 97 having a central opening therein. Thus when cannula 24 is inserted inwardly within "O" ring 94, collar 90, "O" ring 95, sleeve 96 and washer 97, upon the tightening of nut 30, the "O" rings are compressed against cannula 24 and form seals against the same.

An elongated longitudinal bore 98 lies within cannula 24 and has a side opening 99 that communicates with openings 92 and 93 in spool 90. The unique side opening 99 interaction with the double "O" ring seals provides a cannula which is easily used. The disposable cannulas are merely inserted into compression fittings 30 and collar 90. The fitting 30 is then tightened to create the necessary seals. It will be seen that when plunger 81 is drawn outwardly to the position shown in FIG. 3, a vacuum is created which extends through the longitudinal opening to balloon 23 and thus keeps the balloon in a collapsed state as found in FIG. 8. Upon being inserted into the uterine cavity, plunger 81 is depressed and locked into position through slot 84 engaging the edge of housing 20 and thus balloon 23 is expanded to the condition shown in FIGS. 1, 5, and 9. Upon a slight withdrawal of cannula 24 and balloon 22, the end of the device will assume the position which is found in FIG. 9.

Returning now to FIGS. 12 through 14, with the instrument having the balloon 23 and cannula 24 inserted in the uterine cavity and with the instrument charged with carbon dioxide gas as previously described, the next step is to discharge the gas into the uterine cavity so that a determination may be made as to the patency of the Fallopian tube canals. Upon pressing an end cap 100 secured to the end of spool valve 27 by suitable means such as screws, the spool valve is urged until it reaches the condition shown in FIG. 14 wherein an opposite end cap 101 is extended from its position in FIG. 13. Upon spool valve 27 assuming the position of FIG. 14 another spool or reduced diameter portion 102 communicates with passage 55 and 104. Portion 102 is defined through the use of another "O" ring 103 disposed in an annular groove between "O" ring 57 and valve cap 100. In this condition, the carbon dioxide gas in chamber 44 passes through the passageway 55 and communicates with another passageway 104. That is, the carbon dioxide gas is then passed through passageway 104 and further communicates with a central longitudinal passageway 105 formed in cannula 24. The emerging orifice 106 is formed transversely beyond the end of balloon 23 in cannula 24 so that the opening communicates with fallopian tubes 62 and 63 in the uterine cavity 71. In some sitautions it may also be desirable to curve the end of cannula 24. It will be further noted that when spool valve 27 is in the position shown in FIG. 14, that is, when the carbon dioxide gas is released through passageways 55 and passageways 104 through 106, it is impossible for someone to attempt to charge the system. Thus if any gas is applied to check valve 25, it will be blocked from movement through passage 50 upon reaching spool valve 27.

Depending upon the condition of the fallopian tubes, the amount of carbon dioxide escaping into the uterine cavity may be measured and upon measuring the amount of carbon dioxide that escapes into the peritoneal cavity, a determination may then be made as to whether or not the fallopian tube are "Open", partially occluded or completed "Closed."

In operation, the discharged instrument 20 is fitted with a new cannula 24. Gas charge mechanism 26 complete with capsule 45, is fitted to check valve 25 until the device is fully charged. Any attempt to recharge the device will cause the spring to compress until "O" ring 41 no longer seals and overpressure is released. The device automatically works like a pressure relief valve insuring that the pressure of gas applied through the instrument is never greater than the designed pressure. The spring counteracts against gas within chamber 44. Since aging springs only weaken, the construction insures that the pressure delivered by the device will never increase due to a component failure.

After charging, the indicator 32 moves to the position shown as "charged" in FIG. 1. Balloon 23 is evacuated by withdrawing piston 86 and plunger 22 as shown in FIG. 3. The instrument is then inserted toward the uterine cavity as shown in FIGS. 8 and 9 until the balloon portion is situated within the cervix. Balloon 23 is then expanded by depressing and locking piston 22. Markings on the shaft of cannula 24 assist in determining proper placement of the balloon. Once inflated, the balloon seals the uterine cavity from the vaginal cavity. The seal is effective up to a pressure of about 250 mm Hg. The relatively thick, rigid balloon deforms the walls of the cervix in forming the seal. The balloon is not capable of expanding toward fundus 74 or over opening 106. It is constructed and arranged to exert a sealing pressure against the cervix rather than to be a deformable balloon which would squeeze into the uterine cavity when filled with sufficient gas. Spool valve 27 is moved to the test position by depressing end cap 100. Approximately 55 cubic centimeters of carbon dioxide are available to be introduced into the uterine cavity at a pressure of about 200 mm Hg. through openings 106. As the gas enters the uterine cavity, the volume within chamber 44 decreases, and spring 43 rebounds in an effort to keep a constant pressure of about 200 mm Hg.

If the fallopian tubes are patent, gas escapes from the fallopian tubes 12 to the peritoneal cavity. Spring 43 continues to rebound as the gas leaves chamber 44 until it is completely empty. Pointer 32 assumes the "open" position shown in FIG. 2. If the tubes are occluded, an initial volume of gas is discharged from chamber 44 to uterine cavity 71 until the pressure in cavity 71 is equal to that in chamber 44. The pointer should be then within the range shown as "closed" in FIGS. 1 and 2. A slow leak is indicated by a volume change, not a pressure change. The volume in chamber 44 decreases and spring 43 maintains the pressure. Movement of pointer 32 shows any gas volume change within the instrument and uterine cavity.

Rather than measuring patency by a change in pressure, the device of the invention measures by a volumetric change. Equal pressure is maintained within the instrument and uterine cavity as long as gas is remaining within chamber 44. This overcomes some of the disadvantages inherent in devices which rely on pressure changes. Those devices may provide misleading results if a slow leak is present. In such cases, the relatively resilient uterine walls contract as volume is lost, with little apparent pressure drop. In contrast, the device of the invention maintains the same pressurized distention of the uterine walls during the test and any change is always seen as loss of gas volume.

Upon the test being completed, plunger handle 22 is withdrawn from the instrument, collapsing balloon 23 and permitting the balloon 23 and cannula 24 to be withdrawn from the uterine cavity. It will also be observed that various steps for carrying out the procedural method of determining the patency of the fallopian tubes is established.

In considering this invention, it should be remembered that the present disclosure is illustrative only and the scope of the invention should be determined by the appended claims.

What is claimed is:

1. An instrument for determining patency of Fallopian tubes by tubal insufflation, the instrument comprising:
   (a) housing means constructed and arranged to hold gas under a pressure of less than 200 MM. Hg therewithin;
   (b) gas dispensing means for controllably releasing gas within said housing means to a disposable probe means, said gas dispensing means including spring means comprising a spring which urges a piston through a gas receiving cylinder within said housing means such that pressure is constantly applied to gas within said housing means; said dispensing means further including a patency indicator in operative connection to said spring means such that a change in gas volume within said housing means may be observed on the exterior of said housing means, said gas dispensing means further including valve means for charging and discharging said instrument with gas;
   (c) disposable probe means constructed and arranged for dispensing gas within said instrument to a uterine cavity, said probe means adapted to be connected to said housing means so as to receive gas through said valve means, said probe means further including separate lumens through which patency measuring gas may pass from said housing means out through the probe end beyond said expandable member, said probe including a second lumen which communicates with the interior of said expandable member and with means for collapsing and expanding said expandable member and
   (d) means for collapsing and expanding said expandable member, said means being constructed and arranged to include a piston and cylinder which may alternatively force air into or out of said expandable member when a probe is connected to said housing means which carries the collapsing and expanding means.

2. An instrument for tubal insufflation of the Fallopian tubes comprising:
   (a) housing means constructed and arranged to hold gas under pressure therewithin;
   (b) gas dispensing means for controllably releasing gas within said housing means to a disposable probe means, said gas dispensing means including spring means having a spring which urges a piston through a gas receiving cylinder within said housing means such that pressure is constantly applied to gas within said housing means, said dispensing means further including a patency indicator in operative connection with said spring means such that a change in gas volume within said housing means may be observed on the exterior of said housing means, said gas dispensing means further including valve means for charging and discharging said instrument with gas;
   (c) disposable probe means constructed and arranged for dispensing gas within said instrument to a uterine cavity, said probe means adapted to be connected to said housing means so as to receive gas through said valve means, said probe means including an expandable member adjacent its remote end, said expandable member including means such that inflation of said expandable member while inserted within a cervix will provide a seal against pressure of up to about 250 mm Hg, said probe including a central lumen through which gas passes from said housing means; and
   (d) gas charging means for charging gas into said housing means, said gas charging means and said gas dispensing means including means such that said gas charging means will not function when said gas dispensing means is operated so as to provide a fail-safe mechanism.

3. An apparatus for tubal insufflation of the Fallopian tubes of a female animal to determine patency comprising:
   (a) housing means carrying gas dispensing control means and expansion control means;
   (b) disposable probe means adapted to be connected to said housing means, said probe means carrying an expandable means at one end thereof and including first and second conduits, the second conduit being in fluid communication with said expandable means and said expansion control means, said expandable means and probe means including means positionable in the uterine cavity of a female and when expanded by said expansion control means, said expansion means being able to seal the opening to said cavity when so positioned;
   (c) said gas dispensing control means and said housing means being constructed and arranged such that a quantity of gas may be held within said housing means until released to said first conduit which communicates to the end of said probe means beyond said expandable means, said gas dispensing means including spring means which when released urges said gas within said housing through said first conduit, and said dispensing means further including a patency indicator in operative connection to said spring means such that a volumetric change of gas within said housing may be observed on the exterior of said housing means, so as to indicate the patency condition of a female and;
   (d) gas charging means for charging gas into said housing means, said gas charging means and said gas dispensing means including means such that said gas charging means will not function when said gas dispensing means is operated so as to provide a fail-safe mechanism.

4. The instrument of claim 1 wherein said means for collapsing said expandable member and said gas dispensing means, are two separate and discrete means.

5. The instrument of claim 1 wherein said housing mens has a predetermined capacity of substantially 55 cubic centimeters at about a pressure of about 200 mm of mercury.

6. The instrument of claim 2 wherein said patency indicator has a moving member and an indicia scale, said moving member indicating the condition of said dispensing means in terms of the openness of the fallopian tube canals.

7. The instrument of claim 6 wherein said probe means includes an elongated cannula having a longitudinal opening extending the length of said cannula communicating with said expandable member.

8. The instrument of claim 1 wherein said means communicating with, and collapsing and expanding said expandable memer includes pump means vented to the atmosphere.

9. The instrument of claim 8 wherein said pump means is manually controlled and operated.

10. The instrument of claim 2 wherein said valve means includes a portion communicating with said gas dispensing means including a check valve means, so that said gas dispensing means is incapable of receiving gas when in a dispensing position.

11. The instrument of claim 7 wherein said elongated cannula has a curved end to accommodate easy insertion of the same through the cervical opening into the uterine cavity.

12. The instrument of claim 10 including:
a separate and distinct source of pressurized carbon dioxide having an orifice constructed and arranged to charge said gas dispensing means through said check valve means.

* * * * *